US007494972B2

(12) United States Patent
Stern et al.

(10) Patent No.: US 7,494,972 B2
(45) Date of Patent: *Feb. 24, 2009

(54) METHOD FOR INHIBITING ACCELERATED ATHEROSCLEROSIS IN A SUBJECT SUFFERING FROM HYPERCHOLESTEROLEMIA OR HYPERTRIGLYCERIDEMIA

(75) Inventors: David Stern, Great Neck, NY (US); Ann Marie Schmidt, Franklin Lakes, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 93 days.

This patent is subject to a terminal disclaimer.

(21) Appl. No.: 11/319,949

(22) Filed: Dec. 27, 2005

(65) Prior Publication Data
US 2007/0099829 A1 May 3, 2007

Related U.S. Application Data

(63) Continuation of application No. 08/905,709, filed on Aug. 5, 1997, now Pat. No. 7,101,838.

(51) Int. Cl.
*A61K 38/00* (2006.01)
*C07K 14/00* (2006.01)
(52) U.S. Cl. .............................. 514/2; 530/300; 530/350
(58) Field of Classification Search ........................ None
See application file for complete search history.

(56) References Cited

U.S. PATENT DOCUMENTS

| 5,585,344 | A | 12/1996 | Vlassara et al. |
| 5,688,653 | A | 11/1997 | Ulrich et al. |
| 5,864,018 | A | 1/1999 | Morser et al. |
| 6,555,651 | B2 | 4/2003 | Stern et al. |
| 7,101,838 | B2 | 9/2006 | Stern et al. |

FOREIGN PATENT DOCUMENTS

| WO | WO/97/26813 | 7/1997 |
| WO | WO/97/26913 | 7/1997 |
| WO | WO/97/39121 | 10/1997 |
| WO | WO/97/39125 | 10/1997 |
| WO | WO/98/22138 | 5/1998 |
| WO | WO/99/07402 | 2/1999 |
| WO | WO/99/18987 | 4/1999 |
| WO | WO/01/12598 | 2/2001 |

OTHER PUBLICATIONS

Basha et al., Atheroscl. 131: 1192-1202, 1995.*
Mickle et al., Med. Clin. North Am., vol. 84(3), p. 597-607, 2000.*
Adelhorst et al., J. Biol. Chem. 269: 6275-6278, 1994.*
U.S. Appl. No. 09/374,214, filed Aug. 13, 1999, David Stern, et al.
U.S. Appl. No. 08/592,070, filed Jan. 26, 1996, David Stern, et al.

Brett, J., et al. "Survey of the distribution of a newly-characterized receptor for AGEs in tissues" Am. J. Pathol. 143:1699-1712 (1993).
Connolly, E.S., et al. "Procedural and strain-related variables significantly affect outcome in a murine model of focal cerebral ischemia" Neurosurg. 38:523-532 (1996).
Gibbons, G.H. and Dzau, V.J. "Molecular therapies for vascular diseases" Science 272:689-693 (1996).
Hori, et al. "The Receptor for Advanced Glycation Endproducts: Implications for the Development of Diabetic Vascular Disease. Fundam. Clin. Cardiol." In: The Endothelium in Clinical Practice. Chapter 11, pp. 311-329 (Jan. 1997).
Khoury, J., et al. "Macrophages adhere to glucose-modified basement membrane via their scavenger receptors" J. Biol. Chem. 269:10197-10200 (1994).
Kindy, M.S. and Rader D.J. "Reduction in Amyloid A Amyloid Formation in Apolipoprotein-E-Deficient Mice" American Journal of Pathology 152:1387-1395 (1998).
Marui, N., et al. "VCAM-1 gene transcription and expression are regulated through an oxidant-sensitive mechanism in human vascular endothelial cells" J. Clin. Invest. 92:1866-1874 (1993).
Nakamura, Y. et al., "Immunohistochemical localization of advanced glycation endproducts in coronary atheroma and cardiac tissue in diabetes mellitus" Am. J. Pathol. 143(6):1649-1656 (1993).
Nakashima, Y., et al. "ApoE-deficient mice develop lesions of all phases of atherosclerosis throughout the arterial tree" Arteriolscler. Thromb. 141:133-140 (1994).
Palinski, W., et al. "Imunological evidence for the presence of advanced glycation end products in atherosclerotic lesions of euglycemic rabbits" Arteriolscl. Thromb. And Vasc. Biol. 15(5):571-582 (1995).
Park, L., et al. "Suppression of accelerated diabetic atherosclerosis by soluble Receptor for AGE (sRAGE)" Nature Medicine 4:1025-1031 (1998).
Park, L., et al. "A murine model of accelerated diabetic atherosclerosis: suppression by soluble receptor for advanced glycation endproducts" Circulation Supplement. Abstract 3079 (1997).
Ritthaler, et al. "Expression of receptors for advanced glycation end products in peripheral occlusive vascular disease" Am. J. Path. 146:688-694 (1995).
Schmidt, A.M., et al. "Regulation of human mononuclear phagocyte migration by cell surface-binding proteins for advanced glycation end products" J. Clin. Invest. 92:2155-2168 (1993).

(Continued)

*Primary Examiner*—Robert Landsman
*Assistant Examiner*—Gyan Chandra
(74) *Attorney, Agent, or Firm*—John P. White; Cooper & Dunham LLP

(57) ABSTRACT

The present invention provides for a method to prevent accelerated atherosclerosis in a subject predisposed thereto which comprises administering to the subject a polypeptide derived from soluble receptor for advanced glycation endproduct in an amount effective to prevent accelerated atherosclerosis in the subject. The present invention also provides for a method to prevent a macrovessel disease in a subject predisposed thereto which comprises administering to the subject a polypeptide derived from soluble receptor for advanced glycation endproduct in an amount effective to prevent macrovessel disease in the subject.

12 Claims, 5 Drawing Sheets

OTHER PUBLICATIONS

Schmidt, A.M., et al. "The V-Domain of Receptor for Advanced Glycation Endproducts (RAGE) mediates binding of AGEs: a novel target for therapy of diabetes" Circulation Supplement 96(194):1-37 (1997).

Schmidt, A.M., et al. "Activation of RAGE: a mechanism for chronic dysfunction in diabetic vasculopathy and atherosclerosis" Circ. Res. 84:489-497 (1999).

Vlassara, H., et al. "Identification of Galectin-2 as a high affinity binding protein for Advanced Glycation Endproducts (AGE): a new member of the AGE-Receptor complex" Molecular Medicine 1:634-646 (1995).

Vlassara, H., et al. "Pathogenic effects of advanced glycosylation: biochemical, biologic, and clinical implications for diabetes and aging" Lab. Invest. 70:138-151 (1994).

Wautier, J.L., et al. "Interaction of diabetic erythrocytes bearing advanced glycation endproducts with the endothelial receptor AGE induces generation of reactive oxygen intermediates and cellular dysfunction" Circulation Supplement 94(8): #4139 (1996).

Yan. S.D., et al. "Enhanced cellular oxidant stress by the interaction of advanced glycation endproducts with their receptors/binding proteins" J. Biol. Chem. 269:9889-9897 (1994).

International Search Report issued on Nov. 4, 1998 in connection with PCT Publication No. WO/1999/007402.

Written Opinion issued on Jun. 21, 1999 in connection with PCT Publication No. WO/1999/007402.

International Preliminary Examination Report issued Nov. 30, 1999 in connection with PCT Publication No. WO/1999/007402.

Oct. 1, 1998 Office Action issued in connection with U.S. Appl. No. 08/905,709, now U.S. Patent No. 7,101,838.

Jun. 24, 1999 Office Action issued in connection with U.S. Appl. No. 08/905,709, now U.S. Patent No. 7,101,838.

Nov. 12, 1999 Advisory Action issued in connection with U.S. Appl. No. 08/905,709, now U.S. Patent No. 7,101,838.

Jun. 15, 2000 Final Office Action issued in connection with U.S. Appl. No. 08/905,709, now U.S. Patent No. 7,101,838.

Feb. 12, 2001 Notice of Allowance and Issue Fee Due issued in connection with U.S. Appl. No. 08/905,709, now U.S. Patent No. 7,101,838.

Jun. 29, 2001 Office Action issued in connection with U.S. Appl. No. 08/905,709, now U.S. Patent No. 7,101,838.

Apr. 23, 2002 Final Office Action issued in connection with U.S. Appl. No. 08/905,709, now U.S. Patent No. 7,101,838.

Oct. 7, 2002 Advisory Action issued in connection with U.S. Appl. No. 08/905,709, now U.S. Patent No. 7,101,838.

May 7, 2003 Office Action issued in connection with U.S. Appl. No. 08/905,709, now U.S. Patent No. 7,101,838.

Nov. 12, 2003 Final Office Action issued in connection with U.S. Appl. No. 08/905,709, now U.S. Patent No. 7,101,838.

Mar. 9, 2004 Advisory Action issued in connection with U.S. Appl. No. 08/905,709, now U.S. Patent No. 7,101,838.

Mar. 18, 2005 Office Action issued in connection with U.S. Appl. No. 08/905,709, now U.S. Patent No. 7,101,838.

Sep. 26, 2005 Notice of Allowance issued in connection with U.S. Appl. No. 08/905,709, now U.S. Patent No. 7,101,838.

Written Opinion issued Dec. 26, 2001 in connection with PCT Publication No. WO/2001/012598.

International Preliminary Examination Report issued Apr. 19, 2002 in connection with PCT Publication No. WO/2001/012598.

International Search Report issued Jun. 22, 2001 in connection with PCT Publication No. WO/2001/012598.

Supplementary Partial European Search Report issued Feb. 21, 2005 in connection with European Patent Application No. 00955464.3, national stage of PCT Publication No. WO/2001/012598.

Communication Pursuant to Article 96(2) EPC issued May 2, 2005 in connection with European Patent Application No. 00955464.3, national stage of PCT Publication No. WO/2001/012598.

Communication Pursuant to Article 96(2) EPC issued Nov. 29, 2006 in connection with European Patent Application No. 00955464.3, national stage of PCT Publication No. WO/2001/012598.

Mar. 26, 2001 Office Action issued in connection with U.S. Appl. No. 09/374,214.

Jul. 5, 2001 Office Action issued in connection with U.S. Appl. No. 09/374,214.

Apr. 9, 2002 Office Action issued in connection with U.S. Appl. No. 09/374,214.

Nov. 19, 2003 Final Office Action issued in connection with U.S. Appl. No. 09/374,214.

Apr. 10, 2003 Advisory Action issued in connection with U.S. Appl. No. 09/374,214.

Jul. 2, 2004 Office Action issued in connection with U.S. Appl. No. 09/374,214.

Feb. 10, 2005 Notice of Allowance and Fee(s) Due issued in connection with U.S. Appl. No. 09/374,214.

Sep. 14, 2006 Office Action issued in connection with U.S. Appl. No. 09/374,214.

International Search Report issued May 19, 1997 in connection with PCT Publication No. WO/1997/026813.

Written Opinion issued Nov. 19, 1997 in connection with PCT Publication No. WO/1997/026813.

International Preliminary Examination Report issued Apr. 23, 1999 in connection with PCT Publication No. WO/1997/026813.

International Search Report issued Feb. 2, 1999 in connection with PCT Publication No. WO/1999/018987.

Written Opinion issued Oct. 12, 1999 in connection with PCT Publication No. WO/1999/018987.

Written Opinion issued Nov. 16, 1999 in connection with PCT Publication No. WO/1999/018987.

International Preliminary Examination Report issued Mar. 14, 2000 in connection with PCT Publication No. WO/1999/018987.

Dec. 20, 1996 Office Action issued in connection with U.S. Appl. No. 08/592,070.

Jul. 8, 1997 Office Action issued in connection with U.S. Appl. No. 08/592,070.

May 13, 1998 Office Action issued in connection with U.S. Appl. No. 08/592,070.

Dec. 28, 1998 Office Action issued in connection with U.S. Appl. No. 08/592,070.

Aug. 3, 1999 Final Office Action issued in connection with U.S. Appl. No. 08/592,070.

Mar. 9, 2000 Advisory Action issued in connection with U.S. Appl. No. 08/592,070.

Jun. 21, 2000 Office Action issued in connection with U.S. Appl. No. 08/592,070.

Mar. 13, 2001 Final Office Action issued in connection with U.S. Appl. No. 08/592,070.

Dec. 17, 2003 Office Action issued in connection with U.S. Appl. No. 08/592,070.

Jun. 16, 2004 Final Office Action issued in connection with U.S. Appl. No. 08/592,070.

Sep. 21, 2004 Advisory Action issued in connection with U.S. Appl. No. 08/592,070.

Oct. 17, 2005 Final Office Action issued in connection with U.S. Appl. No. 08/592,070.

Mar. 9, 2006 Advisory Action issued in connection with U.S. Appl. No. 08/592,070.

Sep. 18, 2006 Final Office Action issued in connection with U.S. Appl. No. 08/592,070.

Aug. 25, 1998 Office Action issued in connection with U.S. Appl. No. 08/948,131, now U.S. Patent No. 6,555,651.

Jan. 25, 1999 Office Action issued in connection with U.S. Appl. No. 08/948,131, now U.S. Patent No. 6,555,651.

Dec. 20, 1999 Office Action issued in connection with U.S. Appl. No. 08/948,131, now U.S. Patent No. 6,555,651.

Sep. 11, 2000 Final Office Action issued in connection with U.S. Appl. No. 08/948,131, now U.S. Patent No. 6,555,651.

Jul. 26, 2001 Office Action issued in connection with U.S. Appl. No. 08/948,131, now U.S. Patent No. 6,555,651.

Feb. 8, 2002 Office Action issued in connection with U.S. Appl. No. 08/948,131, now U.S. Patent No. 6,555,651.

Nov. 5, 2002 Notice of Allowance and Fee(s) Due issued in connection with U.S. Appl. No. 08/948,131, now U.S. Patent No. 6,555,651.

Supplementary Partial European Search Report issued Nov. 6, 2002 in connection with European Patent Application No. 98952294.0, regional stage of PCT Publication No. WO/1999/018987.

Supplementary Partial European Search Report issued Jan. 31, 2003 in connection with European Patent Application No. 98952294.0, regional stage of PCT Publication No. WO/1999/018987.

Communication Pursuant to Article 96(2) EPC issued Apr. 11, 2005 in connection with European Patent Application No. 98952294.0, regional stage of PCT Publication No. WO/1999/018987.

Communication Pursuant to Article 96(2) EPC issued May 14, 2007 in connection with European Patent Application No. 98952294.0, regional stage of PCT Publication No. WO/1999/018987.

Aug. 29, 2005 Office Action issued in connection with U.S. Appl. No. 10/049,893, national stage of PCT Publication No. WO/2001/012598.

Nov. 9, 2005 Office Action issued in connection with U.S. Appl. No. 10/049,893, national stage of PCT Publication No. WO/2001/012598.

Jan. 31, 2006 Office Action issued in connection with U.S. Appl. No. 10/049,893, national stage of PCT Publication No. WO/2001/012598.

Jul. 17, 2006 Final Office Action issued in connection with U.S. Appl. No. 10/049,893, national stage of PCT Publication No. WO/2001/012598.

Oct. 13, 2006 Advisory Action issued in connection with U.S. Appl. No. 10/049,893, national stage of PCT Publication No. WO/2001/012598.

Dec. 13, 2006 Office Action issued in connection with U.S. Appl. No. 10/049,893, national stage of PCT Publication No. WO/2001/012598.

Brownlee M. Glycation products and the pathogenesis of diabetic complications. Diab. Care 15(12):1835-1842, 1992.

Neeper M, AM Schmidt, J Brett, SD Yan, F Wang, YC Pan, K Elliston, D Stern and A Shaw. Cloning and expression of RAGE: a cell surface receptor for advanced glycosylation end products of proteins. J. Biol. Chem. 267:14998-15004, 1992.

Schmidt AM, M Vianna, M Gerlach, J Brett, J Ryan, J Kao, C Esposito, H Hegarty, W Hurley, M Clauss, F Wang, YC Pan, TC Tsang, and D Stern. Isolation and characterization of binding proteins for advanced glycosylation end products from lung tissue which are present on the endothelial cell surface. J. Biol. Chem. 267:14987-14997, 1992.

Schmidt AM, O Hori, J Brett, SD Yan, JL Wautier, and D Stern. Cellular receptors for advanced glycation endproducts: implications for induction of oxidant stress and cellular dysfunction in the pathogenesis of vascular lesions. Arterioscl. And Thromb. 14:1521-1528, 1994.

Schmidt AM, SD Yan, and D Stern. The dark side of glucose(News and Views). Nat. Med. 1:1002-1004, 1995.

Schmidt AM, M Hasu, D Popov, JH Zhang, SD Yan, J Brett, R Cao, K Kuwabara, G Costache, N Simionescu, and D Stern. The receptor for Advanced Glycation Endproducts(RAGE) has a central role in vessel wall interactions and gene activation in response to AGEs in the intravascular space. PNAS(USA) 91:8807-8811, 1994.

Wautier JL, C Zoukourian, O Chappey, MP Wautier, PJ Guillausseau, R Cao, O Hori, D Stern, and AM Schmidt. Recepter-mediated endothelial cell dysfunction in diabetic vasculopathy: soluble receptor for advanced glycation endproducts blocks hyperpermeability. J. Clin. Invest. 97:238-243, 1996.

May 23, 2001 Office Action issued in connection with U.S. Appl. No. 09/498,459.

Jan. 11, 2002 Office Action in connection with U.S. Appl. No. 09/498,459.

Sep. 26, 2002 Final Office Action issued in connection with U.S. Appl. No. 09/498,459.

So, W.Y., et al. "Genetics of type 2 diabetes mellitus", Hong Kong Medical Journal 6:66-76 (2000).

Vlassara, H., et al. "Diabetes and advanced glycation endproducts", J. Int. Med. 251:87-101 (2002).

Dec. 23, 2003 Office Action issued in connection with U.S. Appl. No. 09/498,459.

Jun. 8, 2004 Final Office Action issued in connection with U.S. Appl. No. 09/498,459.

Aug. 30, 2004 Advisory Action issued in connection with U.S. Appl. No. 09/498,459.

Sep. 12, 2005 Office Action issued in connection with U.S. Appl. No. 09/498,459.

Apr. 18, 2006 Final Office Action issued in connection with U.S. Appl. No. 09/498,459.

Nov. 13, 2006 Advisory Action issued in connection with U.S. Appl. No. 09/498,459.

Jan. 30, 2007 Office Action issued in connection with U.S. Appl. No. 09/498,459.

Mickle, et al., "Genotype-phenotype relationships in cystic fibrosis", Med. Clin. North Am. 84(3):597-607 (May 2000).

Voet, et al., Biochemistry, John Wiley & Sons, Inc. 126-129 and 228-234 (1990).

Yan, et al., "Two-amino acid molecular switch in an epithelial morphogen that regulates binding to two distinct receptors", Science 290:523-527 (2000).

Nov. 7, 2007 Final Office Action issued in connection with U.S. Appl. No. 09/498,459.

May 28, 2008 Office Action issued in connection with U.S. Appl. No. 10/049,893, national stage of PCT Publication No. WO 2001/012598.

* cited by examiner

FIG. 1A      FIG. 1B

FIG. 3A        FIG. 3B

FIG. 4A

```
   1 CGGAGAAGGATGGCAGCAGGGGCAGTGGTCGGAGCCTGGATGCTAGTCCTCAGTCTGGGG   60
                M  A  A  G  A  V  V  G  A  W  M  L  V  L  S  L  G

61 GGGACAGTCACGGGGGACCAAAACATCACAGCCCGGATCGGGAAGCCACTGGTGCTGAAC  120
     G  T  V  T  G  D  Q  N  I  T  A  R  I  G  K  P  L  V  L  N

121 TGCAAGGGAGCCCCCAAGAAACCACCCCAGCAGCTGGAATGGAAACTGAACACAGGCCGG  180
     C  K  G  A  P  K  K  P  P  Q  Q  L  E  W  K  L  N  T  G  R

181 ACAGAAGCTTGGAAAGTCCTGTCTCCCCAGGGAGACCCCTGGGATAGCGTGGCTCGGGTC  240
     T  E  A  W  K  V  L  S  P  Q  G  D  P  W  D  S  V  A  R  V

241 CTCCCCAACGGCTCCCTCCTCCTGCCGGCTGTTGGGATCCAGGATGAGGGGACTTTCCGG  300
     L  P  N  G  S  L  L  L  P  A  V  G  I  Q  D  E  G  T  F  R

301 TGCCGGGCAACGAGCCGGAGCGGAAAGGAGACCAAGTCTAACTACCGAGTCGAGTCTAT   360
     C  R  A  T  S  R  S  G  K  E  T  K  S  N  Y  R  V  R  V  Y

361 CAGATTCCTGGGAAGCCAGAAATTGTTGATCCTGCCTCTGAACTCATGGCTGGTGTCCC   420
     Q  I  P  G  K  P  E  I  V  D  P  A  S  E  L  M  A  G  V  P

421 AATAAGGTGGGGACATGTGTGTCCGAGGGGGGCTACCCTGCAGGGACTCTTAACTGGCTC  480
     N  K  V  G  T  C  V  S  E  G  G  Y  P  A  G  T  L  N  W  L

481 TTGGATGGGAAAACTCTGATTCCTGATGGCAAAGGAGTGTCAGTGAAGGAAGAGACCAAG  540
     L  D  G  K  T  L  I  P  D  G  K  G  V  S  V  K  E  E  T  K

541 AGACACCCAAAGACAGGGCTTTTCACGCTCCATTCGGAGCTGATGGTGACCCCAGCTCGG  600
     R  H  P  K  T  G  L  F  T  L  H  S  E  L  M  V  T  P  A  R

601 GGAGGAGCTCTCCACCCCACCTTCTCCTGTAGCTTCACCCCTGGCCTTCCCCGGCGCCGA  660
     G  G  A  L  H  P  T  F  S  C  S  F  T  P  G  L  P  R  R  R

661 GCCCTGCACACGGCCCCCATCCAGCTCAGGGTCTGGAGTGAGCACCGAGGTGGGGAGGGC  720
     A  L  H  T  A  P  I  Q  L  R  V  W  S  E  H  R  G  G  E  G

721 CCCAACGTGGACGCTGTGCCACTGAAGGAAGTCCAGTTGGTGGTAGAGCCAGAAGGGCA   780
     P  N  V  D  A  V  P  L  K  E  V  Q  L  V  V  E  P  E  G  G

781 GCAGTAGCTCCTGGTGGTACTGTGACCTTGACCTGTGAAGCCCCGGCCCAGCCCCCACCT  840
     A  V  A  P  G  G  T  V  T  L  T  C  E  A  P  A  Q  P  P  P

841 CAAATCCACTGGATCAAGGATGGCAGCCCCTGCCCCTTCCCCCTGGCCCCATGCTGCTC   900
     Q  I  H  W  I  K  D  G  R  P  L  P  L  P  P  G  P  M  L  L

901 CTCCCAGAGGTAGGGCCTGAGGACCAGGGAACCTACAGTTGTGTGGCCACCCATCCCAGC  960
     L  P  E  V  G  P  E  D  Q  G  T  Y  S  C  V  A  T  H  P  S

961 CATGGGCCCCAGGAGAGCCGTGCTGTCAGCGTCACGATCATCGAAACAGGCGAGGAGGG  1020
     H  G  P  Q  E  S  R  A  V  S  V  T  I  I  E  T  G  E  E  G

1021 ACGACTGCAGGCTCTGTGGAAGGGCCGGGGCTGGAAACCCTAGCCCTGACCCTGGGGATC  1080
     T  T  A  G  S  V  E  G  P  G  L  E  T  L  A  L  T  L  G  I

1081 CTGGGAGGCCTGGGGACAGTGGCCCTGCTCATTGGGGTCATCGTGTGGCATCGAAGGCGG  1140
     L  G  G  L  G  T  V  A  L  L  I  G  V  I  V  W  H  R  R  R

1141 CAACGCAAAGGACAGGAGAGGAAGGTCCCGGAAAACCAGGAGGAGGAAGAGGAGGAGAGA  1200
     Q  R  K  G  Q  E  R  K  V  P  E  N  Q  E  E  E  E  E  R

1201 GCGGAACTGAACCAGCCAGAGGAGCCCGAGGCGGCAGAGAGCAGCACAGGAGGGCCTTGA  1260
     A  E  L  N  Q  P  E  E  P  E  A  A  E  S  S  T  G  G  P  *

1261 GGAGCCCACGGCCAGACCCGATCCATCAGCCCCTTTTCTTTTCCCACACTCTGTTCTGGC  1320

1321 CCCAGACCAGTTCTCCTCTGTATAATCTCCAGCCCACATCTCCCAAACTTTCTTCCACAA  1380

1381 CCAGAGCCTCCCACAAAAAGTGATGAGTAAACACCTGCCACATTTAAAAAAAAAAAAAAA  1440
```

FIG. 4B

```
  1 GGGCCAGCCCGAACAGCAGTTGGAGCCTGGGTGCTGGTCCTCAGTCTGTGGGGGCAGTA   60
     G  A  A  G  T  A  V  G  A  W  V  L  V  L  S  L  W  G  A  V

61 GTAGGTGCTCAAAACATCACAGCCCGGATTGGCGAGCCACTGGTGCTGAAGTGTAAGGGG  120
     V  G  A  Q  N  I  T  A  R  I  G  E  P  L  V  L  K  C  K  G

121 GCCCCCAAGAAACCACCCCAGCGGCTGGAATGGAAACTGAACACAGGCCGGACAGAAGCT  180
     A  P  K  K  P  P  Q  R  L  E  W  K  L  N  T  G  R  T  E  A

181 TGGAAGGTCCTGTCTCCCCAGGGAGGAGGCCCCTGGGACAGTGTGGCTCGTGTCCTTCCC  240
     W  K  V  L  S  P  Q  G  G  G  P  W  D  S  V  A  R  V  L  P

241 AACGGCTCCCTCTTCCTTCCGGCTGTCGGGATCCAGGATGAGGGGATTTTCCGGTGCAGG  300
     N  G  S  L  F  L  P  A  V  G  I  Q  D  E  G  I  F  R  C  R

301 GCAATGAACAGGAATGGAAAGGAGACCAAGTCCAACTACCGAGTCCGTGTCTACCAGATT  360
     A  M  N  R  N  G  K  E  T  K  S  N  Y  R  V  R  V  Y  Q  I

361 CCTGGGAAGCCAGAAATTGTAGATTCTGCCTCTGAACTCACGGCTGGTGTTCCCAATAAG  420
     P  G  K  P  E  I  V  D  S  A  S  E  L  T  A  G  V  P  N  K

421 GTGGGGACATGTGTGTCAGAGGGAAGCTACCCTGCAGGGACTCTTAGCTGGCACTTGGAT  480
     V  G  T  C  V  S  E  G  S  Y  P  A  G  T  L  S  W  H  L  D

481 GGGAAGCCCCTGGTGCCTAATGAGAAGGGAGTATCTGTGAAGGAACAGACCAGGAGACAC  540
     G  K  P  L  V  P  N  E  K  G  V  S  V  K  E  Q  T  R  R  H

541 CCTGAGACAGGGCTCTTCACACTGCAGTCGGAGCTAATGGTGACCCCAGCCCGGGGAGGA  600
     P  E  T  G  L  F  T  L  Q  S  E  L  M  V  T  P  A  R  G  G

601 GATCCCCGTCCCACCTTCTCCTGTAGCTTCAGCCCAGGCCTTCCCCGACACCGGGCCTTG  660
     D  P  R  P  T  F  S  C  S  F  S  P  G  L  P  R  H  R  A  L

661 CGCACAGCCCCCATCCAGCCCGTGTCTGGGAGCCTGTGCCTCTGGAGGAGGTCCAATTG   720
     R  T  A  P  I  Q  P  R  V  W  E  P  V  P  L  E  E  V  Q  L

721 GTGGTGGAGCCAGAAGGTGGAGCAGTAGCTCCTGGTGGAACCGTAACCCTGACCTGTGAA  780
     V  V  E  P  E  G  G  A  V  A  P  G  G  T  V  T  L  T  C  E

781 GTCCCTGCCCAGCCCTCTCCTCAAATCCACTGGATGAAGGATGGTGTGCCCTTGCCCCTT  840
     V  P  A  Q  P  S  P  Q  I  H  W  M  K  D  G  V  P  L  P  L

841 CCCCCCAGCCCTGTGCTGATCCTCCCTGAGATAGGGCCTCAGGACCAGGGAACCTACAGC  900
     P  P  S  P  V  L  I  L  P  E  I  G  P  Q  D  Q  G  T  Y  S

901 TGTGTGGCCACCCATTCCAGCCACGGGCCCCAGGAAAGCCGTGCTGTCAGCATCAGCATC  960
     C  V  A  T  H  S  S  H  G  P  Q  E  S  R  A  V  S  I  S  I

961 ATCGAACCAGGCGAGGAGGGGCCAACTGCAGGCTCTGTGGGAGGATCAGGGCTGGGAACT 1020
     I  E  P  G  E  E  G  P  T  A  G  S  V  G  G  S  G  L  G  T

1021 CTAGCCCTGGCCCTGGGGATCCTGGGAGGCCTGGGGACAGCCGCCCTGCTCATTGGGGTC 1080
     L  A  L  A  L  G  I  L  G  G  L  G  T  A  A  L  L  I  G  V

1081 ATCTTGTGGCAAAGGCGGCAACGCCGAGGAGAGGAGAGGAAGGCCCCAGAAAACCAGGAG 1140
     I  L  W  Q  R  R  Q  R  R  G  E  E  R  K  A  P  E  N  Q  E

1141 GAAGAGGAGGAGCGTGCAGAACTGAATCAGTCGGAGGAACCTGAGGCAGGCGAGAGTAGT 1200
     E  E  E  E  R  A  E  L  N  Q  S  E  E  P  E  A  G  E  S  S

1201 ACTGGAGGGCCTTGAGGGGCCCACAGACAGATCCCATCCATCAGCTCCCTTTTCTTTTTC 1260
     T  G  G  P  *

1261 CCTTGAACTGTTCTGGCCTCAGACCAACTCTCTCCTGTATAATCTCTCTCCTGTATAACC 1320

1321 CCACCTTGCCAAGCTTTCTTCTACAACCAGAGCCCCCCACAATGATGATTAAACACCTGA 1380

1381 CACATCTTGCAAAAAAAAAAAAAAAAA 1406
```

```
                         SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 1438 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 1:

CGGAGAAGGA TGGCAGCAGG GGCAGTGGTC GGAGCCTGGA TGCTAGTCCT CAGTCTGGGG         60

GGGACAGTCA CGGGGGACCA AAACATCACA GCCCGGATCG GGAAGCCACT GGTGCTGAAC        120

TGCAAGGGAG CCCCCAAGAA ACCACCCCAG CAGCTGGAAT GGAAACTGAA CACAGGCCGG        180

ACAGAAGCTT GGAAAGTCCT GTCTCCCCAG GGAGACCCCT GGGATAGCGT GGCTCGGGTC        240

CTCCCCAACG GCTCCCTCCT CCTGCCGGCT GTTGGGATCC AGGATGAGGG GACTTTCCGG        300

TGCCGGGCAA CGAGCCGGAG CGGAAAGGAG ACCAAGTCTA ACTACCGAGT CCGAGTCTAT        360

CAGATTCCTG GGAAGCCAGA AATTGTTGAT CCTGCCTCTG AACTCATGGC TGGTGTCCCC        420

AATAAGGTGG GGACATGTGT GTCCGAGGGG GGCTACCCTG CAGGGACTCT TAACTGGCTC        480

TTGGATGGGA AACTCTGATT CCTGATGGCA AAGGAGTGTC AGTGAAGGAA GAGACCAAGA        540

GACACCCAAA GACAGGGCTT TTCACTCTCC ATTCGGAGCT GATGGTGACC CCAGCTCGGG        600

GAGGAGCTCT CCACCCCACC TTCTCCTGTA GCTTCACCCC TGGCCTTCCC CGGCGCCGAG        660
```

-continued

| | |
|---|---|
| CCCTGCACAC GGCCCCCATC CAGCTCAGGG TCTGGAGTGA GCACCGAGGT GGGGAGGGCC | 720 |
| CCAACGTGGA CGCTGTGCCA CTGAAGGAAG TCCAGTTGTG GTAGAGCCAG AAGGGGGAGC | 780 |
| AGTAGCTCCT GGTGGTACTG TGACCTTGAC CTGTGAAGCC CCCGCCCAGC CCCCACCTCA | 840 |
| AATCCACTGG ATCAAGGATG GCAGGCCCCT GCCCCTTCCC CCTGGCCCCA TGCTGCTCCT | 900 |
| CCCAGAGGTA GGGCCTGAGG ACCAGGGAAC CTACAGTTGT GTGGCCACCC ATCCCAGCCA | 960 |
| TGGGGGGGAG GAGAGCCGTG CTGTCAGCGT CACGATCATC GAAACAGGCG AGGAGGGGAC | 1020 |
| GACTGCAGGC TCTGTGGAAG GGCCGGGGCT GGAAACCTAG CCCTGACCCT GGGGATCCTG | 1080 |
| GGAGGCCTGG GGACAGTCGC CCTGCTCATT GGGGTCATCG TGTGGCATCG AAGGCCGGCA | 1140 |
| ACGCAAAGGA CAGGAGAGGA AGGTCCCGGA AAACCAGGAG GAGGAAGAGG AGGAGAGAGC | 1200 |
| GGAACTGAAC CAGCCAGAGG AGCCCGAGGC GGCAGAGAGC AGCACAGGAG GGCCTTGAGG | 1260 |
| AGCCCACGGC CAGACCCGAT CCATCAGCCC CTTTTCTTTT CCCACACTCT GTTCTGGCCC | 1320 |
| CAGACCAGTT CTCCTCTGTA TAATCTCCAG CCCACATCTC CCAAACTTTC TTCCACAACC | 1380 |
| AGAGCCTCCC ACAAAAAGTG ATGAGTAAAC ACCTGCCACA TTTAAAAAAA AAAAAAAA | 1438 |

(2) INFORMATION FOR SEQ ID NO: 2:

(i) SEQUENCE CHARACTERISTICS:
        (A) LENGTH: 119 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "AMINO ACID"

(xi) SEQUENCE DESCRIPTION: SEQ ID NO: 2:

| | |
|---|---|
| AAGAGAGGTT GTAGCGATGT AGAGAGGTCA TGATGAAGGT CGGAGTGTGG TTGTTAGGAT | 60 |
| CTGATAGGGA GGAAGGTTTC AAGGGGTCAT GATTGGTTAG GGTATGGGGT AGGAAATGG | 119 |

(2) INFORMATION FOR SEQ ID NO: 3:

(i) SEQUENCE CHARACTERISTICS:
        (A) LENGTH: 1405 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO: 3:

| | |
|---|---|
| GGGGCAGCCG GAACAGCAGT TGGAGCCTGG GTGCTGGTCC TCAGTCTGTG GGGGCAGTA | 60 |
| GTAGGTGCTC AAAACATCAC AGCCCGGATT GGCGAGCCAC TGGTGCTGAA GTGTAAGGGG | 120 |
| GCCCCCAAGA AACCACCCCA GCGGCTGGAA TGGAAACTGA ACACAGGCCG ACAGAAGCT | 180 |
| TGGAAGGTCC TGTCTCCCCA GGGAGGAGGC CCCTGGGACA GTGTGGCTCG TGTCCTTCCC | 240 |
| AACGGCTCCC TCTTCCTTCC GGCTGTCGGG ATCCAGGATG AGGGGATTTT CCGGTGCAGG | 300 |
| GCAATGAACA GGAATGGAAA GGAGACCAAG TCCAACTACC GAGTCCGTGT CTACCAGATT | 360 |
| CCTGGGAAGC CAGAAATTGT AGATTCTGCC TCTGAACTCA CGGCTGGTGT TCCCAATAAG | 420 |
| GTGGGGACAT GTGTGTCAGA GGGAAGCTAC CCTGCAGGGA CTCTTAGCTG GCACTTGGAT | 480 |
| GGGAAGCCCC TGGTGCCTAA TGAGAAGGGA GTATCTGTGA AGGAACGAC CAGGAGACAC | 540 |
| CCTGAGACAG GGCTCTTCAC ACTGCAGTCG GAGCTAATGG TGACCCCAGC CGGGGAGGA | 600 |
| GATCCCCGTC CCACCTTCTC CTGTAGCTTC AGCCCAGGCC TTCCCCGACA CCGGGCCTTG | 660 |

-continued

```
CGCACAGCCC CCATCCAGCC CCGTGTCTGG GAGCCTGTGC CTCTGGAGGA GGTCCAATTG      720

GGTGGTGGAG CCAGAAGGTG GAGCAGTAGC TCCTGGTGGA ACCGTAACCC TGACCTGTGA      780

AGTCCCTGCC CAGCCCTCTC CTCAAATCCA CTGGATGAAG GATGGTGTGC CCTGCCCCTT      840

CCCCCCAGCC CTGTGCTGAT CCTCCCTGAG ATAGGGCCTC AGGACCAGGG AACCTACAGC      900

TGTGTGGCCA CCCATTCCAG CCACGGGCCC CAGGAAAGCC GTGCTGTCAG CATCAGCATC      960

ATCGAACCAG GCGAGGAGGG GCCAACTGCA GGCTCTGTGG GAGGATCAGG GCTGGGAACT     1020

CTAGCCCTGG CCCTGGGGAT CCTGGGAGGC CTGGGGACAG CCGCCCTGCT CATTGGGGTC     1080

ATCTTGTGGC AAAGGCGGCA ACGCCGAGGA GAGGAGAGGA GGCCCCAGAA AACCAGGAGG     1140

AAGAGGAGGA GCGTGCAGAA CTGAATCAGT CGGAGGAACC TGAGGCAGGC GAGAGTACTA     1200

CTGGAGGGCC TTGAGGGGCC CACAGACAGA TCCCATCCAT CAGCTCCCTT TTCTTTTTCC     1260

CTTGAACTGT TCTGGCCTCA GACCAACTCT CTCCTGTATA ATCTCTCTCC TGTATAACCC     1320

CACCTTGCCA AGCTTTCTTC TACAACCAGA GCCCCCCACA ATGATGATTA AACACCTGAC     1380

ACATCTTTGC AAAAAAAAAA AAAAA                                           1405

(2) INFORMATION FOR SEQ ID NO: 4:

(i) SEQUENCE CHARACTERISTICS:
        (A) LENGTH: 109 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "AMINO ACID"

(xi) SEQUENCE DESCRIPTION: SEQ ID NO: 4:

GAAGAGAGAG ATAGCGATGT AGGGAGAGGC AGTGATAGGT CGAGTGGTTG TTAGGTCGAT       60

AGGAAGGTTT CAGGGTCATG AGGTAGGGGG TAAGGGGTAA GGAAAGTGG                  109
```

US 7,494,972 B2

METHOD FOR INHIBITING ACCELERATED ATHEROSCLEROSIS IN A SUBJECT SUFFERING FROM HYPERCHOLESTEROLEMIA OR HYPERTRIGLYCERIDEMIA

This application is a continuation of U.S. Ser. No. 08/905,709, filed Aug. 5, 1997, now U.S. Pat. No. 7,101,838, issued Sep. 5, 2006, the contents of which are hereby incorporated by reference in their entirety into the present application.

The invention disclosed herein was made with Government support under NIH Grants No. HL56881 and AG00602 from the Department of Health and Human Services. Accordingly, the U.S. Government has certain rights in this invention.

BACKGROUND OF THE INVENTION

Throughout this application, various publications are referenced by author and date within the text. Full citations for these publications may be found listed alphabetically at the end of the specification immediately following the Sequence Listing and before the claims. The disclosures of these publications in their entireties are hereby incorporated by reference into this application in order to more fully describe the state of the art as known to those skilled therein as of the date of the invention described and claimed herein.

Ischemic heart disease is a leading cause of morbidity and mortality in the general population, but especially in patients with diabetes. The prevalence of coronary artery disease is as high as 55% in adult patients with diabetes (Robertson and Strong, 1968). Indeed, data from the Framingham Heart Study demonstrate that mortality from cardiovascular disease in non-insulin dependent diabetes (NIDDM) is more that doubled in diabetic men and more than quadrupled in diabetic women when compared to nondiabetic control subjects (Kannel and McGee, 1979). In addition to increased prevalence, studies have shown that atherosclerosis in diabetic patients is clearly more accelerated and extensive. In one autopsy series, for example, patients with diabetes were found to have more severe disease of the left anterior descending coronary artery (Waller et al., 1980), a higher incidence of two and three-vessel disease (Crall and Roberts, 1978), and a greater diffuseness of distribution of atherosclerotic lesions (Hamby et al., 1976). The findings were confirmed by coronary angioplasty in symptomatic patients (Pyorala et al., 1978).

The reasons for accelerated atherosclerosis in the setting of diabetes are numerous. However, even after correction for dyslipidemia, hypertension and obesity, multivariate analysis studies have indicated that diabetic patients have an excess risk of cardiovascular disease relative to nondiabetic subjects (Kannel and McGee, 1979). For example, in the Nurses' Health Study of 1,500 diabetic subjects among a total of 115,000 women, the incidence of cardiovascular disease was 5-fold higher in the diabetic subjects regardless of their levels of cholesterol (Manson et al., 1991). The data suggest that factors unique to the diabetic population play an important role.

SUMMARY OF THE INVENTION

The present invention provides for a method to prevent accelerated atherosclerosis in a subject predisposed thereto which comprises administering to the subject a polypeptide derived from soluble receptor for advanced glycation endproduct in an amount effective to prevent accelerated atherosclerosis in the subject. The present invention also provides for a method to prevent a macrovessel disease in a subject predisposed thereto which comprises administering to the subject a polypeptide derived from soluble receptor for advanced glycation endproduct in an amount effective to prevent macrovessel disease in the subject.

BRIEF DESCRIPTION OF THE FIGURES

FIGS. 3A, 3B. Gross appearance of the proximal aorta of diabetic apolipoprotein E (0) mice treated with mouse serum albumin (left panel) or soluble mouse RAGE (right panel) under dissection microscopy. Apolipoprotein E (0) mice were rendered diabetic with stz. After 2 wks of diabetes, mice were treated with either sRAGE (20 mg/day, intraperitoneally) or equimolar amounts of mouse serum albumin (40 µg/day, intraperitoneally) for 6 more wks. Gross inspection of the proximal aorta revealed nearly complete absence of lesions in the second and third branches of the proximal aorta in mice treated with sRAGE compared to those treated with mouse serum albumin. Marked decrease in lesions at the first branch point and at the arch of the aorta were also observed in sRAGE-treated mice.

FIGS. 4A-B. Nucleotide and Amino Acid Sequence of Bovine and Human RAGE. The bovine (FIG. 4A) and human (FIG. 4B) genes were sequenced by the dideoxy chain termination method. Potential N-linked glycosylation sites are indicated by boxed sequences, the putative polyadenylation sites are shown with bold underlining, and sequences matching the sequenced bovine peptides are indicated by light underlining. The following amino acid residues from the underlined peptide sequences were not determined by protein sequencing: all Cys (C) and Trpo (W), Asn25 (N25) and Glu50 (E50). The bovine nucleotide sequence is SEQ. ID. NO:1. The bovine amino acid sequence is SEQ. ID. NO:2. The human nucleotide sequence is SEQ. ID. NO:3. The human amino acid sequence is SEQ. ID. NO:4.

DETAILED DESCRIPTION OF THE INVENTION

Figure 1:
FIGS. 1A, 1B. Gross appearance of the proximal aorta of apolipoprotein E(0) nice under dissection microscopy. Aortic specimens were subjected to retrograde injection of methylene blue in apolipoprotein E(0) mice with diabetes (16 wk old mice; 10 wks diabetes, FIG. 1A) or age-matched nondiabetic controls (16 wk old, FIG. 1B).

The present invention provides for a method to prevent accelerated atherosclerosis in a subject predisposed thereto which comprises administering to the subject a polypeptide derived from soluble receptor for advanced glycation endproduct in an amount effective to prevent accelerated atherosclerosis in the subject.

The subject may be a mammal. The mammal may be a human. The subject may be a diabetic subject. The subject may be suffering from an apolipoprotein deficiency, or from hyperlipidemia. The hyperlipidemia may be hypercholesterolemia or hypertriglyceridemia. The subject may have a glucose metabolism disorder. The subject may be an obese subject.

In one embodiment of the invention, the polypeptide may comprise at least a portion of naturally occurring soluble receptor for advanced glycation endproduct. The polypeptide may comprise a "V" domain of naturally occurring soluble receptor for advanced glycation endproduct. The polypeptide may comprise a 10 kilodalton domain of naturally occurring soluble receptor for advanced glycation endproduct.

The polypeptide may comprise a sequence less than or equal to 20 amino acids in length which sequence is within the sequence of the naturally occurring soluble receptor for advanced glycation endproduct. For example, the sequence may be 5 amino acids in length, 3 amino acids in length, 8 amino acids in length or 11 amino acids in length. The length may also be any other length between 2 and 20 amino acids. In one embodiment of the invention, the length may be one amino acid.

The polypeptide may be a peptidomimetic, a synthetic polypeptide or a polypeptide analog. The polypeptide may be a non-natural polypeptide which has chirality not found in nature, i.e. D-amino acids or L-amino acids.

In another embodiment of the present invention, the method may further comprise administering to the subject a pharmaceutically acceptable carrier during the administration of the polypeptide. The administration may comprise intralesional, intraperitoneal, intramuscular or intravenous injection; infusion; liposome-mediated delivery; or topical, nasal, oral, ocular or otic delivery.

The polypeptide may be delivered hourly, daily, weekly, monthly, yearly (e.g. in a time release form) or as a one time delivery. The delivery may be continuous delivery for a period of time, e.g. intravenous delivery.

The effective amount of the polypeptide may comprise from about 0.000001 mg/kg body weight to about 100 mg/kg body weight. In one embodiment, the effective amount may comprise from about 0.001 mg/kg body weight to about 50 mg/kg body weight. In another embodiment, the effective amount may range from about 0.01 mg/kg body weight to about 10 mg/kg body weight. The actual effective amount will be based upon the size of the polypeptide, the biodegradability of the polypeptide, the bioactivity of the polypeptide and the bioavailability of the polypeptide. If the polypeptide does not degrade quickly, is bioavailable and highly active, a smaller amount will be required to be effective. The effective amount will be known to one of skill in the art; it will also be dependent upon the form of the polypeptide, the size of the polypeptide and the bioactivity of the polypeptide. One of skill in the art could routinely perform empirical activity tests for a polypeptide to determine the bioactivity in bioassays and thus determine the effective amount.

The present invention also provides for a method to prevent a macrovessel disease in a subject predisposed thereto which comprises administering to the subject a polypeptide derived from soluble receptor for advanced glycation endproduct in an amount effective to prevent macrovessel disease in the subject.

The subject may be a human or an animal. The subject may be a diabetic subject. The subject may be suffering from an apolipoprotein deficiency. The subject may be suffering from hyperlipidemia. The hyperlipidemia may be hypercholesterolemia or hypertriglyceridemia. The subject may have a glucose metabolism disorder. The subject may be an obese subject.

In one embodiment of the invention, the polypeptide comprises at least a portion of naturally occurring soluble receptor for advanced glycation endproduct (RAGE). The polypeptide may comprise a "V" domain of naturally occurring soluble receptor for advanced glycation endproduct.

The polypeptide may comprise a 10 kilodalton domain of naturally occurring soluble receptor for advanced glycation endproduct. The polypeptide may comprises less than or equal to 20 amino in length which sequence is within the sequence of the naturally occurring soluble receptor for advanced glycation endproduct.

The polypeptide may be a peptidomimetic, a synthetic polypeptide or a polypeptide analog.

In another embodiment of the present invention, the method may further comprise administering a pharmaceutically acceptable carrier to the subject during the administration of the polypeptide.

The administration may comprise intralesional, intraperitoneal, intramuscular or intravenous injection; infusion; liposome-mediated delivery; or topical, nasal, oral, ocular or otic delivery.

The sRAGE polypeptide may be administered hourly, daily, weekly, monthly, yearly (e.g. in a time release form) or as a one time delivery. The delivery or administration may be continuous delivery for a period of time, e.g. intravenous delivery.

The following abbreviations are used herein: AGE—advanced glycation endproduct(s); RAGE—receptor for advanced glycation endprocut(s); sRAGE—soluble receptor for advanced glycation endproduct(s).

The polypeptide may be a peptide, a peptidomimetic, a synthetic polypeptide, a derivative of a natural polypeptide, a modified polypeptide, a labelled polypeptide, or a polypeptide which includes non-natural peptides. The peptidomimetic may be identified from screening large libraries of different compounds which are peptidomimetics to determine a compound which is capable of preventing accelerated atherosclerosis in a subject predisposed thereto.

The polypeptide may be a derivative of soluble receptor for advanced glycation end product (sRAGE). The polypeptide may be a soluble extracellular portion of a receptor for advanced glycation end product, an antibody or portion thereof, wherein the antibody is capable of specifically binding to the receptor for advanced glycation endproduct. The antibody may be a monoclonal antibody or a polyclonal antibody. A portion of the antibody may be a Fab or a complementarity determining region or a variable region. The polypeptide may be capable of specifically binding to the amyloid-β peptide. The polypeptide may bind to the amyloid-β peptide at the site where the receptor for advanced glycation end product interacts.

In addition to naturally-occurring forms of polypeptides derived from sRAGE, the present invention also embraces other sRAGE polypeptides such as polypeptide analogs of sRAGE. Such analogs include fragments of sRAGE. Following the procedures of the published application by Alton et al. (WO 83/04053), one can readily design and manufacture genes coding for microbial expression of polypeptides having primary conformations which differ from that herein specified for in terms of the identity or location of one or more residues (e.g., substitutions, terminal and intermediate additions and deletions). Alternately, modifications of cDNA and genomic genes can be readily accomplished by well-known site-directed mutagenesis techniques and employed to generate analogs and derivatives of sRAGE polypeptide. Such products share at least one of the biological properties of sRAGE but may differ in others. As examples, products of the invention include those which are foreshortened by e.g., deletions; or those which are more stable to hydrolysis (and, therefore, may have more pronounced or longerlasting effects than naturally-occurring); or which have been altered to delete or to add one or more potential sites for O-glycosylation and/or N-glycosylation or which have one or more cysteine residues deleted or replaced by e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within sRAGE, which fragments may possess one property of sRAGE and not others. It is noteworthy that activity is not necessary for any one or more of the polypeptides of the invention to have therapeutic utility or utility in other contexts, such as in assays of sRAGE antagonism. Competitive antagonists may be quite useful in, for example, cases of overproduction of sRAGE.

Of applicability to polypeptide analogs of the invention are reports of the immunological property of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically-significant proteins such as viral antigens, polypeptide hormones, and the like. Included among the immune reactions of such polypeptides is the provocation of the formation of specific antibodies in immunologically-active animals [Lerner et al., *Cell,* 23, 309-310 (1981); Ross et al., *Nature,* 294, 654-658 (1981); Walter et al., *Proc. Natl. Acad. Sci. USA,* 7, 4882-4886 (1981); Wong et al., *Proc. Natl. Sci. USA,* 79, 5322-5326 (1982); Baron et al., Cell, 28, 395-404 (1982); Dressman et al., Nature, 295, 185-160 (1982); and Lerner, Scientific American, 248, 66-74 (1983). See also, Kaiser et al. [Science, 223, 249-255 (1984)] relating to biological and immunological properties of synthetic peptides which approximately share secondary structures of peptide hormones but may not share their primary structural conformation. The polypeptide of the present invention may be a peptidomimetic compound which may be at least partially unnatural. The peptidomimetic compound may be a small molecule mimic of a portion of the amino acid sequence of sRAGE. The compound may have increased stability, efficacy, potency and bioavailability by virtue of the mimic. Further, the compound may have decreased toxicity. The peptidomimetic compound may have enhanced mucosal intestinal permeability. The compound may be synthetically prepared.

The compound of the present invention may include L-, D- or unnatural amino acids, alpha, alpha-disubstituted amino acids, N-alkyl amino acids, lactic acid (an isoelectronic analog of alanine). The peptide backbone of the compound may have at least one bond replaced with PSI-[CH—CH] (Kempf et al. 1991). The compound may further include trifluorotyrosine, p-Cl-phenylalanine, p-Br-phenylalanine, poly-L-propargylglycine, poly-D,L-allyl glycine, or poly-L-allyl glycine.

One embodiment of the present invention is a peptidomimetic compound having the biological activity of preventing accelerated athersclerosis in a subject wherein the compound has a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl), N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

The subject may be a mammal or non-mammal. The subject may be a human. The subject may be a mouse, a cow, a monkey, a horse, a pig, or a dog. The subject may be a diabetic subject. The subject may be suffering from an apolipoprotein deficiency. The subject may have a glucose metabolism disorder. The subject may be an obese subject. The subject may have genetically-mediated or diet-induced hyperlipidemia. AGEs form in lipid-enriched environments even in euglycemia.

The administration in this embodiment may be intralesional, intraperitoneal, intramuscular or intravenous injection; infusion; liposome-mediated delivery; topical, nasal, oral, anal, ocular or otic delivery. The administration may be constant for a certain period of time or periodic and at specific intervals.

The carrier may be a diluent, an aerosol, a topical carrier, an aqeuous solution, a nonaqueous solution or a solid carrier.

In the practice of any of the methods of the invention or preparation of any of the pharmaceutical compositions a therapeutically effective amounts is an amount which is capable of preventing accelerated atherosclerosis in a subject predisposed thereto. Accordingly, the effective amount will vary with the subject being treated, as well as the condition to be treated. For the purposes of this invention, the methods of administration are to include, but are not limited to, administration cutaneously, subcutaneously, intravenously, parenterally, orally, topically, or by aerosol.

As used herein, the term "suitable pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

This invention also provides for pharmaceutical compositions including therapeutically effective amounts of polypeptide compositions and compounds, capable of preventing accelerated, atherosclerosis in a subject by inhibiting the binding of an amyloid-β peptide with a receptor for advanced glycation endproduct, together with suitable diluents, preservatives, solubilizers, emulsifiers, adjuvants and/or carriers. Such compositions may be liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts.

Such compositions will influence the physical state, solubility, stability, rate of in vivo release, and rate of in vivo clearance of the compound or composition. The choice of compositions will depend on the physical and chemical properties of the compound capable of preventing accelerated atherosclerosis in a subject predisposed thereto.

Controlled or sustained release compositions include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Portions of the polypeptide or composition of the invention may be "labeled" by association with a detectable marker substance (e.g., radiolabeled with $^{125}$I or biotinylated) to provide reagents useful in detection and quantification of compound or its receptor bearing cells or its derivatives in solid tissue and fluid samples such as blood, cerebral spinal fluid or urine.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The polypeptide or composition of the present invention may be delivered in a microencapsulation device so as to reduce or prevent an host immune response against the polypeptide or against cells which may produce the polypeptide. The polypeptide or composition of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

Clinical Aspects

In one embodiment of the present invention, the subject may be suffering from clinical aspects as described hereinbelow and as further described in Harper's Biochemistry, R. K. Murray, et al. (Editors) 21st Edition, (1988) Appelton & Lange, East Norwalk, Conn. Such clinical aspects may predispose the subject to atherosclerosis or to accelerated atherosclerosis. Thus, such subjects would benefit from the administration of a polypeptide derived from sRAGE in an effective amount over an effective time.

The subject of the present invention may demonstrate clinical signs of atherosclerosis, hypercholesterolemia or other disorders as discussed hereinbelow.

Clinically, hypercholesterolemia may be treated by interrupting the enterohepatic circulation of bile acids. It is reported that significant reductions of plasma cholesterol can be effected by this procedure, which can be accomplished by the use of cholestyramine resin or surgically by the ileal exclusion operations. Both procedures cause a block in the reabsorption of bile acids. Then, because of release from feedback regulation normally exerted by bile acids, the conversion of cholesterol to bile acids is greatly enhanced in an effort to maintain the pool of bile acids. LDL (low density lipoprotein) receptors in the liver are up-regulated, causing increased uptake of LDL with consequent lowering of plasma cholesterol.

Cholesterol, Atherosclerosis, and Coronary Heart Disease

Many investigators have demonstrated a correlation between raised serum lipid levels and the incidence of coronary heart disease and atherosclerosis in humans. Of the serum lipids, cholesterol has been the one most often singled out as being chiefly concerned in the relationship. However, other parameters—such as serum triacylglycerol concentration—show similar correlations. Patients with arterial disease can have any one of the following abnormalities: (1) elevated concentrations of VLDL (very low density lipoproteins) with normal concentrations of LDL; (2) elevated LDL with Normal VLDL; (3) elevation of both lipoprotein fractions. There is also an inverse relationship between HDL (high density lipoproteins)($HDL_2$) concentrations and coronary heart disease, and some consider that the most predictive relationship is the LDL:HDL cholesterol ratio. This relationship is explainable in terms of the proposed roles of LDL in transporting cholesterol to the tissues and of HDL acting as the scavenger of cholesterol.

Atherosclerosis is characterized by the deposition of cholesterol and cholesteryl eater of lipoproteins containing apo-B-100 in the connective tissue of the arterial walls. Diseases in which prolonged elevated levels of VLDL, IDL, or LDL occur in the blood (e.g., diabetes, mellitus, lipid nephrosis, hypothyroidism, and other conditions of hyperlipidemia) are often accompanied by premature or more sever atherosclerosis.

Experiments on the induction of atherosclerosis in animals indicate a wide species variation in susceptibility. The rabbit, pig, monkey, and humans are species in which atherosclerosis can be induced by feeding cholesterol. The rat, dog, mouse and cat are resistant. Thyroidectomy or treatment with thiouracil drugs will allow induction of atherosclerosis in the dog and rat. Low blood cholesterol is a characteristic of hyperthyroidism.

Hereditary factors play the greatest role in determining individual blood cholesterol concentrations, but of the dietary and environmental factors that lower blood cholesterol, the substitution in the diet of polyunsaturated fatty acids for some of the saturated fatty acids has been the most intensely studied.

Naturally occurring oils that contain a high proportion of linoleic acid are beneficial in lowering plasma cholesterol and include peanut, cottonseed, corn, and soybean oil whereas butterfat, beef fat, and coconut oil, containing a high proportion of saturated fatty acids, raise the level. Sucrose and fructose have a greater effect in raising blood lipids, particularly triacylglycerols, than do other carbohydrates.

The reason for the cholesterol-lowering effect of polyunsaturated fatty acids is still not clear. However, several hypotheses have been advanced to explain the effect, including the stimulation of cholesterol excretion into the intestine and the stimulation of the oxidation of cholesterol to bile acids. It is possible that cholesteryl is esters of polyunsaturated fatty acids are more rapidly metabolized by the liver and other tissues, which might enhance their rate of turnover and excretion. There is other evidence that the effect if largely due to a shift in distribution of cholesterol from the plasma into the tissues because of increased catabolic, rate of LDL. Saturated fatty acids cause the formation of smaller VLDL particles that contain relatively more cholesterol, and they are utilized by extrahepatic tissues at a slower rate than are larger particles. All of these tendencies may be regarded as atherogenic.

Additional factors considered to play a part in coronary heart disease include high blood pressure, smoking, obesity, lack of exercise, and drinking soft as opposed to hard water. Elevation of plasma free fatty acids will also lead to increase VLDL secretion by the liver, involving extra triacylglycerol and cholesterol output into the circulation. Factors leading to higher or fluctuating levels of free fatty acids include emotional stress, nicotine from cigarette smoking, coffee drinking, and partaking of a few large meals rather than more continuous feeding. Premenopausal women appear to be protected against many of these deleterious factors, possibly because they have higher concentrations of HDL than do men and postmenopausal women.

Hypolipidemic Drugs

When dietary measures fail to achieve reduced serum lipid levels, the use of hypolipidemic drugs may be resorted to. Several drugs are known to block the formation of cholesterol at various stages in the biosynthetic pathway. Many of these drugs have harmful effects, but the fungal inhibitors of HMG-CoA reductase, compactin and mevinolin, reduce LDL cholesterol levels with few adverse effects. Sitosterol is a hypocholesterolemic agent that acts by blocking the absorption of cholesterol in the gastrointestinal tract. Resins such as colestipol and cholestyramine (Questran) prevent the reabsorption of bile salts by combining with them, thereby increasing their fecal loss. Neomycin also inhibits reabsorption of bile salts. Clofibrate and gembivrozil exert at least part of their hypolipidemic effect by diverting the hepatic flow of free fatty acids from the pathways of esterification into those of oxidation, thus decreasing the secretion of triacylglycerol and cholesterol containing VLDL by the liver. In addition, they facilitate hydrolysis of VLDL triacylglycerols by lipoprotein lipase. Probucol appears to increase LDL catabolism via receptor-independent pathways. Nicotinic acid reduces the flux of FFA by inhibiting adipose tissue lipolysis, thereby inhibiting VLDL production by the liver.

Disorders of the Plasma Lipoproteins (Dyslipoproteinemias)

A few individuals in the population exhibit inherited defects in their lipoproteins, leading to the primary condition of whether hypo- or hyperlipoproteinemia. Many others having defects such as diabetes mellitus, hypothyroidism, and atherosclerosis show abnormal lipoprotein patterns that are very similar to one or another of the primary inherited conditions. Virtually all of these primary conditions are due to a defect at one or another stage in the course of lipoprotein formation, transport, or destruction. Not all of the abnormalities are harmful.

Hypolipoproteinemia:

1. Abetalipoproteinemia—This is a rare inherited disease characterized by absence of β-lipoprotein (LDL) in plasma. The blood lipids are present in low concentrations—especially acylglycerols, which are virtually absent, since no chylomicrons or VLDL are formed. Both the intestine and the liver accumulate acylglycerols. Abetalipoproteinemia is due to a defect in apoprotein B synthesis.

2. Familial hypobetalipoproteinemia—In hypobetalipoproteinemia, LDL concentration is between 10 and 50% of normal, but chylomicron formation occurs. It must be concluded that apo-B is essential for triacylglycerol transport. Most individuals are healthy and long-lived.

3. Familial alpha-lipoprotein deficiency (Tangier disease)— In the homozygous individual, there is near absence of plasma HDL and accumulation of cholesteryl esters in the tissues. There is no impairment of chylomicron formation or secretion of VLDL by the liver. However, on electrophoresis, there is no pre-β-lipoprotein, but a broad β-band is found containing the endogenous triacylglycerol. This is because the normal pre-β-band contains other apo-proteins normally provided by HDL. Patients tend to develop hypertriacylglycerolemia as a result of the absence of apo-C-II, which normally activates lipoprotein lipase.

Hyperlipoproteinemia:

1. Familial lipoprotein lipase deficiency (type I)—This condition is characterized by very slow clearing of chylomicrons from the circulation, leading to abnormally raised levels of chylomicrons. VLDL may be raised, but there is a decrease in LDL and HDL. Thus, the condition is fat-induced. It may be corrected by reducing the quantity of fat and increasing the proportion of complex carbohydrate in the diet. A variation of this disease is caused by a deficiency in apo-C-II, required as a cofactor for lipoprotein lipase.

2. Familial hypercholesterolemia (type II)-Patients are characterized by hyperbetalipoproteinemia (LDL), which is associated with increased plasma total cholesterol. There may also be a tendency for the VLDL to be elevated in type IIb. Therefore, the patient may have somewhat elevated triacylglycerol levels but the plasma—as is not true in the other types of hyperlipoproteinemia—remains clear. Lipid deposition in the tissue (e.g., xanthomas, atheromas) is common. A type II pattern may also arise as a secondary result of hypothyroidism. The disease appears to be associated with reduced rates of clearance of LDL from the circulation due to defective LDL receptors and is associated with an increased incidence of atherosclerosis. Reduction of dietary cholesterol and saturated fats may be of use in treatment. A disease producing hypercholesterolemia but due to a different cause is Wolman's disease (cholesteryl ester storage disease). This is due to a deficiency of cholesteryl ester hydrolase in lysosomes of cells such as fibroblasts that normally metabolize LDL.

3. Familial type III hyperlipoproteinemia (broad beta disease, remnant removal disease, familial dysbetalipoproteinemia)—This condition is characterized by an increase in both chylomicron and VLDL remnant; these are lipoproteins of density less than 1.019 but appear as a broad β-band on electrophoresis (β-VLDL). They cause hypercholesterolemia and hypertriacylglycerolemia. Xanthomas and atherosclerosis of both peripheral and coronary arteries are present. Treatment by weight reduction and diets containing complex carbohydrates, unsaturated fats, and little cholesterol is recommended. The disease is due to a deficiency in remnant metabolism by the liver caused by an abnormality in apo-E, which is normally present in 3 isoforms, E2, E3, and E4. Patients with type III hyperlipoproteinemia possess only E2, which does not react with the E receptor.

4. Familial hypertriacylglycerolemia (type IV)-This condition is characterized by high levels of endogenously produced triacylglycerol (VLDL). Cholesterol levels rise in proportion to the hypertriacylglycerolemia, and glucose intolerance is frequently present. Both LDL and HDL are subnormal in quantity. This lipoprotein pattern is also commonly associated with coronary heart disease, type II non-insulin-dependent diabetes mellitus, obesity, and many other conditions, including alcoholism and the taking of progestational hormones. Treatment of primary type IV hyperlipoproteinemia is by weight reduction; replacement of soluble diet carbohydrate with complex carbohydrate, unsaturated fat, low-cholesterol diets; and also hypolipidemic agents.

5. Familial type V hyperlipoproteinemia—The lipoprotein pattern is complex, since both chylomicrons and VLDL are elevated, causing both triacylglycerolemia and cholesterolemia. Concentrations of LDL and HDL are low. Xanthomas are frequently present, but the incidence of atherosclerosis is apparently not striking. Glucose tolerance is abnormal and frequently associated with obesity and diabetes. The reason for the condition, which is familial, is not clear. Treatment has consisted of weight reduction followed by a diet not too high in either carbohydrate or fat.

It has been suggested that a further cause of hypolipoproteinemia is overproduction of apo-B, which can influence plasma concentrations of VLDL and LDL.

6. Familial hyperalphalipoproteinemia—This is a rare condition associated with increased concentrations of HDL apparently beneficial to health.

Familial Lecithin Cholesterol Acyltransferase (LCAT) Deficiency: In affected subjects, the plasma concentration of cholesteryl esters and lysolecithin is low, whereas the concentration of cholesterol and lecithin is raised. The plasma tends to be turbid. Abnormalities are also found in the lipoproteins. One HDL fraction contains disk-shaped structures in stacks or rouleaux that are clearly nascent HDL unable to take up cholesterol owing to the absence of LCAT. Also present as an abnormal LDL subfraction is lipoprotein-X, otherwise found only in patients with cholestasis. VLDL are also abnormal, migrating as lipoproteins upon electrophoresis (β-VLDL). Patients with parenchymal liver disease also show a decrease of LCAT activity and abnormalities in the serum lipids and lipoproteins.

Pharmaceutical with Carriers

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable Liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The active ingredient of the present invention (i.e., polypeptide derived from sRAGE, or composition) can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The active ingredient can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Atherosclerosis

In one embodiment of the present invention, the subject may be predisposed to atherosclerosis. This predisposition may include genetic predisposition, environmental predisposition, metabolic predisposition or physical predisposition. There have been recent reviews of atherosclerosis and cardiovascular disease. For example: Keating and Sanguinetti, (May 1996) Molecular Genetic Insights into Cardiovascular Disease, Science 272:681-685 is incorporated by reference in its entirety into the present application. The authors review the application of molecular tools to inherited forms of cardiovascular disease such as arrhythmias, cardiomyopathies, and vascular disease. Table 1 of this reference includes cardiac diseases and the aberrant protein associated with each disease. The diseases listed are: LQT disease, familial hypertrophic cardiomyopathy; duchenne and Becker muscular dystrophy; Barth syndrome Acyl-CoA dehydrogenase deficiencies; mitochondrial disorders; familial hypercholesterolemia; hypobetalipoproteinemia; homocystinuria; Type III hyperlipoproteinemia; supravalvular aortic stenosis; Ehler-Danlos syndrome IV; Marfa syndrome; Heredity hemorrhagic telangiectasia. These conditions are included as possible predispositions of a subject for atherosclerosis.

Furthermore, mouse models of atherosclerosis are reviewed in Breslow (1996) Mouse Models of Atherosclerosis, Science 272:685. This reference is also incorporated by reference in its entirety into the present application. Breslow also includes a table (Table 1) which recites various mouse models and the atherogenic stimulus. For example, mouse models include C57BL/6; Apo E deficiency; ApoE lesion; ApoE R142C; LDL receptor deficiency; and HuBTg. One embodiment of the present invention is wherein a subject has a predisposition to atherosclerosis as shown by the mouse models presented in Breslow's publication.

Gibbons and Dzau review vascular disease in Molecular Therapies for Vascular Disease, Science Vol. 272, pages 689-693. In one embodiment of the present invention, the subject may manifest the pathological events as described in Table 1 of the Gibbons and Dzau publication. For example, the subject may have endothelial dysfunction, endothelial injury, cell activation and phenotypic modulation, dysregulated cell growth, dysregulated apoptosis, thrombosis, plaque rupture, abnormal cell migration or extracellular or intracellular matrix modification.

In another embodiment of the present invention, the subject may have diabetes. The subject may demonstrate complications associated with diabetes. Some examples of such complications include activation of endothelial and macrophage AGE receptors, altered lipoproteins, matrix, and basement membrane proteins; altered contractility and hormone responsiveness of vascular smooth muscle; altered endothelial cell permeability; sorbitol accumulation; neural myoinositol depletion or altered Na-K ATPase activity. Such complications are discussed in a recent publication by Porte and Schwartz, Diabetes Complications: Why is Glucose potentially Toxic?, Science, Vol. 272, pages 699-700.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

Example 1

Supression of Accelerated Diabetic Atherosclerosis by Soluble Receptor for Advanced Glycation Endproducts (sRAGE)

Central to diabetes is the presence of hyperglycemia. An important complication of the interaction of glucose with proteins/lipids is irreversible formation of Advanced Glycation Endproducts, or AGEs (Brownlee, 1992). AGEs accumulate in the plasma and tissues during normal aging, and to an accelerated degree in patients with diabetes. AGEs have been linked to the pathogenesis of diabetic complications.

It has been demonstrated that interaction of AGEs with their cellular receptor RAGE Receptor for AGE) on monocytes and endothelial cells results in the development of a proinflammatory environment in which enhanced monocyte migration/activation, endothelial hyperpermeability, and enhanced expression of adhesion molecules and tissue factor on endothelial cells results in the generation of an environment conducive to the development of vascular lesions (Schmidt et al, 1992; Neeper et al, 1992; Schmidt et al, 1994; Schmidt et al, 1995).

It has also been demonstrated that the extracellular portion of RAGE (called soluble or sRAGE), composed of one "V"-type immunoglobulin domain followed by two "C"-type domains interferes with the ability of AGEs to bind to and activate cellular RAGE (Schmidt et al., 1994). In vivo, administration of sRAGE blocks hyperpermeability in diabetic rats (Wautier et al., 1996).

As discussed hereinbelow, a model of accelerated atherosclerosis in diabetes was developed and used to test the hypothesis that chronic administration of sRAGE ($t_{o/2}$) elimination in diabetic rodents of 22 hrs) prevents the development of accelerated atherosclerosis.

These studies demonstrated that daily intraperitoneal injection of sRAGE prevents the accelerated development of atherosclerosis in apolipoprotein E deficient (or knockout) mice rendered diabetic with streptozotocin.

Materials and Methods:

Animals and the induction of diabetes. Apolipoprotein E(0) mice on the C57B1/6J background (N10; 10 generations backcrossed with >99% homology) were obtained from the Jackson Laboratories. At the age of 7 wks, diabetes was induced in certain male mice with multiple intraperitoneal injections of streptozotocin (55 mg/kg) in 4 daily injections in sterile citrate buffer (0.05M; pH 4.5). Control mice were treated with vehicle (buffer alone). Plasma glucose concentration was then determined with colormetric assay (Sigma®) using blood obtained from the tail vein. Mice were considered diabetic if plasma glucose levels exceeded 300 mg/dl on two separate occasions. All mice were maintained on normal chow diet.

Quantitation of atherosclerotic lesions. Mice were sacrificed at the time points indicated below after induction of diabetes or control treatment. Quantitative analysis of atherosclerotic lesions was performed on sections from the aortic sinus. After humane sacrifice, hearts were fixed in formalin (10%), embedded in gelatin (25%) and frozen. Cryostat sections were cut 10 microns thick, stained with oil red 0 and counterstained with hematoxylin and light green. Fatty lesion area was then determined by computer assisted image analysis (Zeiss Image, Media Cybernetics) in five consecutive sections, each separated by 80 microns. Mean lesion area was quantitated for each group.

Preparation of soluble mouse RAGE. A construct containing mouse soluble RAGE cDNA was prepared and co-transfected with baculovirus DNA according to the manufacturer's instructions (PharMingen). Sf9 cells were then infected with the construct for three days in Grace's insect medium containing fetal bovine serum (10%), followed by three days in Grace's insect medium without serum (Gibco®). At the end of the second three days, cells were separated from supernatant using centrifugation (1,200 rpm×20 mins) and supernatant dialyzed versus buffer containing sodium phosphate (0.02M; pH 7.4) and NaCl (0.05M). After dialysis, supernatant was applied to an SP sepharose resin (5 ml) using the FPLC system (Pharmacia®). Mouse soluble RAGE was eluted using a linear gradient of sodium chloride (0.05M to 0.6M). SDS-PAGE revealed the material to be single-band. Prior to introduction into mice, purified mouse soluble RAGE was passed through an endotoxin-removal column (Detoxigel, Pierce). Final product was devoid of endotoxin as determined by testing in the limulus amebocyte assay (Sigma®), dialyzed versus phosphate-buffered saline and stored in aliquots at 80° C.

Treatment of diabetic mice with soluble RAGE. After induction of diabetes, certain diabetic mice were treated once daily with either soluble mouse RAGE (20 µg/day; intraperitoneally) or with equimolar concentrations of mouse serum albumin (40 µg/day; intraperitoneally) beginning two weeks after induction of diabetes and continuing for six wks. At the end of that time, mice were sacrificed and the aorta subjected to quantitative morphometric analysis of atherosclerotic lesions.

Analysis of lipoproteins. Mice were fasted four hours prior to obtaining plasma for analysis of lipoproteins. Plasma concentrations of cholesterol and triglyceride were measured using commercial kits (Boehringer Mannheim®). VLDL (very low density lipoproteins), IDL (intermediate density lipoproteins)/LDL (low density lipoproteins), and HDL (high density lipoproteins) were separated by density is ultracentrifugation as well as by FPLC.

Results

After treatment with streptozotocin (stz), mean plasma glucose concentration was approximately 350-500 mg/dl, compared with 130-160 mg/dl in controls.

Consistent with previous studies in apo E(0) mice (Plump et al., 1992), fatty streak lesions were observed in both diabetic and control mice at the early time points (4 wks). The lesions first appeared at the aortic root and at the lesser curvature of the arch of the aorta, with progression to each of the principal branches of the thoracic aorta, beginning proximally. At each time point, the lesions were consistently larger in size and more extensive in the diabetic mice compared with the controls. For example, after ten weeks of diabetes, mice demonstrated discrete lesions at each of the thoracic branch points, with nearly complete occlusion of the vessels (FIG. 1B). This was in marked contrast to the age-matched, citrate-treated control mice, in whom only mild fatty streaks, mostly at the aortic root were visualized (FIG. 1A).

Quantitative analysis of the lesions revealed that after eight weeks of diabetes, mean lesion area in the diabetic mice wan approximately 3.7-fold higher than that observed in the nondiabetic controls. Visualization with oil red 0/hematoxylin light green demonstrated advanced atherosclerotic lesions with evidence of fibrous cap formation after 8 weeks of diabetes. A similar experiment revealed an approximately 3-fold increase in mean lesion area after 6 wks of diabetes.

Analysis of lipid profile indicated that induction of diabetes resulted in an approximately 2-fold increase in the levels of VLDL, an approximately 1.4-fold increase in the Levels of LDL and no change in the levels of HDL, compared with citrate-treated control mice. There were no differences in levels of plasma triglyceride between diabetic and nondiabetic mice.

Figure 2:
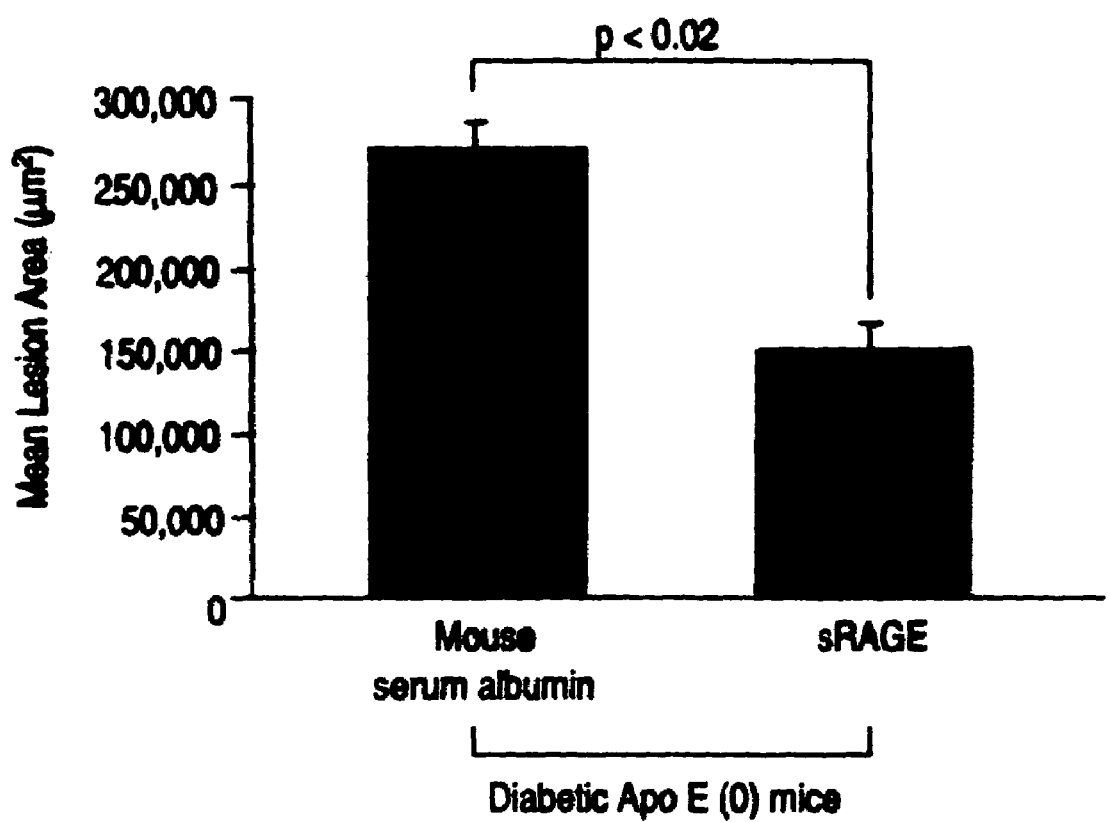
FIG. 2. Treatment of diabetic apolipoprotein E (0) mice with sRAGE suppresses accelerated atherosclerosis. Apolipoprotein E (0) mice were rendered diabetic with stz. After 2 weeks of diabetes, mice were treated with either sRAGE (20 µg/day, intraperitoneally) or equimolar amounts of mouse serum albumin (40 µg/day, intraperitoneally) for 6 more wks. Mean lesion area in diabetic mice treated with sRAGE, 150,046±18,549 µm$^2$ was significantly less than that observed in mice treated with mouse serum albumin, 271,008±16,721 µm$^2$, p, 0.02.

Consistent with the hypothesis as presented herein that enhanced AGE-RAGE interaction was important in the pathogenesis of accelerated atherosclerosis in diabetic mice, treatment of diabetic mice with sRAGE (20%/day; intraperitoneally) resulted in an approximately 1.8-fold decrease in mean lesion area compared with diabetic mice treated with mouse serum albumin, 150,046±18,549 vs. 271,008±16,721 $\mu m^2$, respectively, p<0.02 (FIG. 2). Visual inspection of the aortic tree of a typical diabetic mouse after 8 weeks of diabetes treated with mouse serum albumin revealed evidence of extensive atherosclerotic plaques at the major branch points and at the arch of the aorta FIG. 3A), which were markedly diminished in diabetic mice treated with sRAGE (FIG. 3B). Importantly, mice treated with sRAGE demonstrated no alteration in their levels of plasma glucose. Furthermore, mice treated with sRAGE manifested no differences in lipid profile (total cholesterol, total triglyceride, as well as fractionation of lipoproteins by FPLC analysis), compared with diabetic mice treated with mouse serum albumin. These data suggest that treatment with sRAGE diminished accelerated diabetic atherosclerosis in a glucose- and lipid-independent manner.

Discussion

As detailed herein, the development of one of the first models of accelerated atherosclerosis in a diabetic mouse after treatment with streptozotocin has been demonstrated. Earlier and more advanced atherosclerotic lesions were demonstrated in diabetic mice as compared with age-matched controls.

An important role for enhanced AGE-RAGE interaction in the development of accelerated diabetic atherosclerosis, treatment of diabetic mice with sRAGE, a competitive inhibitor of the interaction of AGEs with cellular RAGE, resulted in a statistically-significant decrease in mean atherosclerotic lesion area after 8 weeks of diabetes.

Taken together, these data indicate that administration of soluble RAGE may be a new and important means by which to prevent chronic complications of diabetes, such as accelerated atherosclerosis.

REFERENCES

Brownlee M. Glycation products and the pathogenesis of diabetic complications. Diab. Care 15(12):1835-1842, 1992.

Carpenter, et al. (1971) Toxicol. Appl. Pharmacol., 18:35-40.

Crall FVJ and WC Roberts. The extramural and intramural coronary arteries in juvenile diabetes mellitus: analysis of nine necropsy patients aged 19 to 38 years with onset of diabetes before age 15 years. Am. J. Med. 64:221-230, 1978.

Hamby R I et al. Reappraisal of the role of the diabetic state in coronary artery disease. Chest 2:251-257, 1976.

Kannel W B and D L McGee. Diabetes and cardiovascular disease: the Framingham study. J. Am. Med. Assoc. 241:2035-2038, 1979.

Kannel W B and D L McGee. Diabetes and glucose tolerance as risk factors for cardiovascular disease: the Framingham study. Diab. Care 2:120-126, 1979.

Manson J E et al. A prospective study of maturity-onset diabetes mellitus and risk of coronary heart disease and stroke in women. Arch. Of. Int. Med. 151:1141-1137, 1991.

Neeper X, A M Schmidt, J Brett, S D Yan, F Wang, Y C Pan, K Elliston, D Stern and A Shaw. Cloning and expression of RAGE: a cell surface receptor for advanced glycocylation end products of proteins. J. Biol. Chem. 267:14998-15004, 1992.

Plump, A S et al. Severe hypercholesterolemia and atherosclerosis in apolipoprotein E-deficient mice created by homologous recombination in ES cells. Cell 71:343-353, 1992.

Pyorala K M, M Laasko and M Uusitupa. Diabetes and atherosclerosis: an epidemiologic view. Diab. Metab. Rev. 3:463-524, 1987.

Robertson W B and J B Strong. Atherosclerosis in persons with hypertension and diabetes mellitus. Lab. Invest. 18:538-551, 1968.

Schmidt A M, M Vianna, M Gerlach, J Brett, J Ryan, J Kao, C Esposito, H Hegarty, W Hurley, M Clause, P Wang, Y C Pan, T C Teang, and D Stern. Isolation and characterization of binding proteins for advanced glycosylation end products from lung tissue which are present on the endothelial cell surface. J. Biol. Chem. 267:14987-14997, 1992.

Schmidt A M, O Hori, J Brett, S D Yan, J L Wautier, and D Stern. Cellular receptors for advanced glycation endproducts: implications for induction of oxidant stress and cellular dysfunction in the pathogenesis of vascular lesions. Arterioscl. And Thromb. 14:1521-1528, 1994.

Schmidt A M, S D Yan, and D Stern. The dark side of glucose (News and Views). Nat. Med. 1:1002-1004, 1995.

Schmidt A M, M Hasu, D Popov, J H Zhang, S D Yan, J Brett, R Cao, K Kuwabara, G Costache, N Simionescu, and D Stern. The receptor for Advanced Glycation Endproducts (RAGE) has a central role in vessel wall interactions and gene activation in response to AGEs in the intravascular space. PNAS(USA) 91:8807-8811, 1994.

Waller B F et al. Status of the coronary arteries at necropsy in diabetes mellitus with onset after age 30 yrs: analysis of 229 diabetic patients with and without clinical evidence of coronary heart disease and comparison to 183 control subjects. Am. J. Med. 69:498-506, 1980.

Wautier J L, C Zoukourian, O Chappey, M P Wautier, P J Guillausseau, R Cao, O Hori, D Stern, and A M Schmidt. Recepter-mediated endothelial cell dysfunction in diabetic vasculopathy: soluble receptor for advanced glycation endproducts blocks hyperpermeability. J. Clin. Invest. 97:238-243, 1996.

What is claimed is:

1. A method for inhibiting accelerated atherosclerosis in a subject suffering from hypercholesterolemia which comprises administering to the subject a pharmaceutical composition comprising a polypeptide comprising a V-type immunoglobulin domain of soluble human receptor for advanced glycation endproduct (sRAGE) followed by two C-type domains of soluble human receptor for advanced glycation endproduct, in an amount effective to inhibit accelerated atherosclerosis in the subject.

2. The method of claim 1, wherein the subject is a mammal.

3. The method of claim 2, wherein the mammal is a human.

4. The method of claim 1, wherein the administration comprises intralesional, intraperitoneal, intramuscular or intravenous injection; infusion; liposome-mediated delivery; or topical, nasal, oral, ocular or otic delivery.

5. The method of claim 1, wherein the polypeptide is administered daily.

6. The method of claim 1, wherein the effective amount of the polypeptide comprises from about 0.000001 mg/kg body weight to about 100 mg/kg body weight.

7. A method for inhibiting accelerated atherosclerosis in a subject suffering from hypertriglyceridemia which comprises administering to the subject a pharmaceutical composition comprising a polypeptide comprising a V-type immunoglobulin domain of soluble human receptor for advanced glycation endproduct followed by two C-type domains of soluble human receptor for advanced glycation endproduct, in an amount effective to inhibit accelerated atherosclerosis in the subject.

8. The method of claim 7, wherein the subject is a mammal.

9. The method of claim 8, wherein the mammal is a human.

10. The method of claim 7, wherein the administration comprises intralesional, intraperitoneal, intramuscular or intravenous injection; infusion; liposome-mediated delivery; or topical, nasal, oral, ocular or otic delivery.

11. The method of claim 7, wherein the polypeptide is administered daily.

12. The method of claim 7, wherein the effective amount of the polypeptide comprises from about 0.000001 mg/kg body weight to about 100 mg/kg body weight.

* * * * *